United States Patent
Weik et al.

(10) Patent No.: US 9,085,640 B2
(45) Date of Patent: Jul. 21, 2015

(54) CARBAMOYLATED EPO-FC FUSION PROTEINS

(75) Inventors: Robert Weik, Hohe Wand-Stollhof (AT); Thomas Hemetsberger, Klosterneuburg (AT); Heinz Redl, Vienne (AT)

(73) Assignee: POLYMUN SCIENTIFIC IMMUNBIOLOGISCHE FORSCHUNG GMBH, Vienna (AT)

( * ) Notice: Subject to any disclaimer, the term of this patent is extended or adjusted under 35 U.S.C. 154(b) by 669 days.

(21) Appl. No.: 12/449,639

(22) PCT Filed: Feb. 20, 2008

(86) PCT No.: PCT/EP2008/001311
§ 371 (c)(1),
(2), (4) Date: Oct. 8, 2009

(87) PCT Pub. No.: WO2008/101680
PCT Pub. Date: Aug. 28, 2008

(65) Prior Publication Data
US 2010/0203050 A1    Aug. 12, 2010

Related U.S. Application Data

(60) Provisional application No. 60/894,948, filed on Mar. 15, 2007.

(30) Foreign Application Priority Data

Feb. 22, 2007    (EP) .................................. 07003659

(51) Int. Cl.
*C07K 14/505*    (2006.01)
*C07K 19/00*    (2006.01)
*A61K 38/18*    (2006.01)

(52) U.S. Cl.
CPC ........... *C07K 14/505* (2013.01); *A61K 38/1816* (2013.01); *C07K 2319/30* (2013.01)

(58) Field of Classification Search
None
See application file for complete search history.

(56) References Cited

FOREIGN PATENT DOCUMENTS

| WO | WO 99/02709 A1 | 1/1999 |
| WO | WO 2005/063808 A1 | 7/2005 |
| WO | WO 2006/002646 A2 | 1/2006 |
| WO | WO 2006/014466 A2 | 2/2006 |
| WO | WO 2007/070983 A1 | 6/2007 |

OTHER PUBLICATIONS

Leist et al., Science, 2004; 305: 239-242.*
Kraus, Kidney Int Suppl, 2001; 78: S102-7—abstract only.*
Tayra et al., Brain Research, 2013; 1502: 55-70.*
Brines, Nature Reviews Neuroscience, 2005; 6: 484-494.*
Hagel, Curr Protoc Mol Biol. May 2001; Chapter 10:Unit 10.9. doi: 10.1002/0471142727.mb1009s44; 32 pages total.*
Doggrell, "A Neuroprotective derivative of Erythropoietin that is not Erythropoietic", Expert Opinion on Investigational Drugs, vol. 13, No. 11, pp. 1517-1519, 2004.
Gorio et al., "Recombinant Human Erythropoietin Counteracts Secondary Injury and Markedly Enhances Neurological Recovery From Experimental Spinal Cord Trauma", Proc. Natl. Acad. Sci., vol. 99, No. 14, pp. 9450-9455, Jul. 9, 2002.
Leist et al., "Derivatives of Erythropoietin that are Tissue Protective but not Erythropoietic", Science, vol. 305, pp. 239-242, Jul. 9, 2004.
Grasso et al., "Erythropoietin and Erythropoietin Receptor Expression after Experimental Spinal Cord Injury Encourages Therapy by Exogenous Erythropoietin", Neurosurgery, vol. 56, No. 4, pp. 821-827, Apr. 2005.
Buddeberg et al., "Behavioral Testing Strategies in a Localized Animal Model of Multiple Sclerosis", Journal of Neuroimmunology, vol. 153, pp. 158-170, 2004.
Savino et al., "Delayed Administration of Erythropoietin and its Non-Erythropoietic Derivatives Ameliorates Chronic Murine Autoimmune Encephalomyelitis", Journal of Neuroimmunology, vol. 172, pp. 27-37, 2006.
Simon et al., "Comparison of carbamylated erythropoietin-FC fusion protein and recombinant human erythropoietin during porcine aortic balloon occlusion-induced spinal cord ischemia/reperfusion injury," Intensive Care Medicine, published online Jul. 16, 2011.
Pavenski et al., "Erythropoietic neuroprotection: Holy Grail or potential to fail?," Intensive Care Medicine, published online Jul. 16, 2011.

* cited by examiner

*Primary Examiner* — Christina Borgeest
(74) *Attorney, Agent, or Firm* — Oliff PLC (57) ABSTRACT

The present invention relates to recombinant fusion proteins wherein erythropoietin (EPO) is linked via its C-terminus to an Fc fragment, and wherein the recombinant fusion proteins are further carbamoylated at the primary amines of the fusion protein. More specifically the invention relates to carbamoylated EPO-Fc fusion proteins, wherein at least one, preferably two or more, lysine amine residues and/or the N-terminal amino acid of the fusion protein are carbamoylated. The carbamoylated EPO-Fc fusion proteins of the present invention having a reduced hematopoietic activity whereas the tissue regenerative activity, i.e. the nerve cell regenerative activity remains unaltered or is even enhanced as compared to unmodified EPO-Fc fusion proteins. The invention further relates to a process for the manufacture of such fusion proteins and to pharmaceutical compositions containing them, as well as to the use of such fusion proteins and pharmaceutical compositions for medical therapy.

23 Claims, 3 Drawing Sheets

SEQUENCE LISTING

<160> NUMBER OF SEQ ID NOS: 4

<210> SEQ ID NO 1
<211> LENGTH: 32
<212> TYPE: DNA
<213> ORGANISM: Artificial Sequence
<220> FEATURE:
<223> OTHER INFORMATION: Synthetic Construct-epo back BamHI primer

<400> SEQUENCE: 1
gggggatccg ccatgggggt gcacgaatgt cc                                32

<210> SEQ ID NO 2
<211> LENGTH: 32
<212> TYPE: DNA
<213> ORGANISM: Artificial Sequence
<220> FEATURE:
<223> OTHER INFORMATION: Synthetic Construct-epo hyb hinge for primer

<400> SEQUENCE: 2
agatttgggc tctctgtccc ctgtcctgca gg                                32

<210> SEQ ID NO 3
<211> LENGTH: 30
<212> TYPE: DNA
<213> ORGANISM: Artificial Sequence
<220> FEATURE:
<223> OTHER INFORMATION: Synthetic Construct-CH3 for NotI primer

<400> SEQUENCE: 3
ggggcggccg ctcatttacc cggagacagg                                   30

<210> SEQ ID NO 4
<211> LENGTH: 30
<212> TYPE: DNA
<213> ORGANISM: Artificial Sequence
<220> FEATURE:
<223> OTHER INFORMATION: Synthetic Construct-hinge hyb epo back primer

<400> SEQUENCE: 4
acaggggaca gagagcccaa atcttgtgac                                   30

CARBAMOYLATED EPO-FC FUSION PROTEINS

TECHNICAL FIELD

The present invention relates to recombinant fusion proteins wherein erythropoietin (EPO) is linked to a protein carrier, more specifically to an antibody or antibody fragment such as an Fc fragment, wherein said recombinant fusion proteins are further carbamoylated. The invention further relates to a process for the manufacture of such fusion proteins and to pharmaceutical compositions containing them, as well as to the use of such fusion proteins and pharmaceutical compositions for medical therapy.

TECHNICAL BACKGROUND

Erythropoietin (EPO), a well known glycoprotein was originally identified for its hormonal effects on the bone marrow and is involved in the growth and development of mature red blood cells. In addition to this hematopoietic activity it has recently been discovered that EPO also functions as a potent, locally produced molecule ameliorating metabolic stress in many tissues. The tissue protective activities of EPO are mediated through interaction with the erythropoietin receptor. In the brain, for example, EPO and its receptor are locally produced, modulated by metabolic stressors, and provide neuroprotective and anti-inflammatory functions (Doggrell, S A. (2004) Expert Opin Investig Drugs; 13(11):1517-9). In the spinal cord, EPO provides beneficial effects including inhibition of apoptosis and necrosis of neurons, oligodendrocytes and endothelial cells, less cavitations, reduction of lipid peroxidation, mobilization of endothelial progenitor cells, promotion of angiogenesis and restoration of vascular autoregulation (Gorio, A. et al (2002) Proc Natl Acad Sci USA; 99(14):9450-5; Leist M. (2004) Science; 305(5681):239-42). EPO has been shown to signal through modulation of members of the nuclear factor (NF)-kappaB pathway as well as by the janus kinase-2/signal transducers and activators of transcription-5 system (Gorio A. (2005) Neurosurgery; 56(4):821-7; Grasso G. (2005) Neurosurgery; 56(4):821-7).

By chemical modification, i.e. carbamoylation of at least one primary amino group of the lysines and/or of the N-terminal amino acid of EPO the hematopoietic activity of this cytokine is considerably reduced while its tissue protective activity, i.e. its nerval cell regenerative activity remains substantially unaltered or is even enhanced as compared to uncarbamoylated EPO.

WO 2006/014466 and WO 2006/002646 disclose the manufacture and use of carbamoylated EPO for various medical indications.

Since EPO has a relatively short serum half-life and since it is well known in the art that the fusion of an immunoglobulin constant region to a non-immuno-globulin protein can markedly prolong the serum half-life of said non-immunoglobulin protein, several approaches have been made linking an immunoglobulin fragment to EPO. For example, WO 99/02709 discloses the production and use of fusion proteins comprising EPO and an Fc portion of an immunoglobulin, wherein the EPO-Fc fusion proteins have an increased in vivo half-life relative to naturally occurring EPO.

From WO2005/063808 it is known that a further improvement of the pharmacokinetics, i.e. prolonged serum half-lives and increased in vivo potency of EPO-Fc fusion proteins can be obtained by mutations, deletions or insertions of specific amino acids.

Accordingly, there is a need for a simplified and less costly EPO therapy, i.e. requiring less frequent EPO administration, for the treatment of diseases, wherein an unaltered or even enhanced tissue regenerative activity, i.e. the nerve cell regenerative activity of EPO, is desirable while simultaneously the hematopoietic activity of EPO is less desirable or is even undesired and shall thus be reduced. Such diseases include but are not limited to malfunctions or impairments of either or both the central (CNS) and peripheral (PNS) nervous systems, and particularly include diseases that are associated with or caused by injuries to the CNS and/or PNS such as physical damages following, for example, a mechanical impact.

SUMMARY OF THE INVENTION

It is thus an objective of the present invention to improve the known EPO-Fc fusion proteins, which have a prolonged serum half-life as compared to unfused EPO proteins, by chemical modification, i.e. carbamoylation, to obtain modified EPO-Fc fusion proteins, which have, in addition to the prolonged serum half-life, a reduced hematopoietic activity but yet an unaltered or enhanced regenerative activity as compared to unmodified EPO-Fc fusion proteins.

The modified EPO-Fc fusion proteins according to the present invention are suitable for the treatment of diseases or malfunctions of either or both the central (CNS) and peripheral (PNS) nervous systems, including diseases that are caused by or associated with physical damage of nerves caused by, for example, mechanical impact, heat or irradiation. It is one of the advantageous features of the modified EPO-Fc fusion proteins of the present invention that they may be administered at higher therapeutic doses as compared to conventional EPO or EPO-Fc for the same purpose, and essentially without augmenting undesired effects on the hematopoietic system, i.e. the blood count.

Accordingly, it is an object of the present invention to provide a modified recombinant EPO fusion protein, wherein EPO is linked to a protein carrier, in particular to an immunoglobulin or immunoglobulin fragment such as an Fc fragment, more particular to the Fc portion of an IgG molecule, and wherein said recombinant fusion protein is further modified by carbamoylation.

It is another object of the invention to provide a method for the preparation of such carbamoylated recombinant EPO-Fc fusion protein.

It is yet another object of the invention to provide pharmaceutical compositions containing such a carbamoylated recombinant EPO-Fc fusion protein.

In yet another aspect the invention relates to the use of such a carbamoylated recombinant EPO-Fc fusion protein for medical therapy.

In yet another aspect the invention relates to the use of pharmaceutical compositions containing such a carbamoylated recombinant EPO-Fc fusion protein for medical therapy.

The principle of the invention is further described in the independent claims, while the various embodiments of the invention are the subject matter of the dependent claims.

BRIEF DESCRIPTION OF THE FIGURE

Ordinate=Beattie-Bresnahan-Basso scale; abscisse=selected time points before and after contusion injury; praeOP=before contusion injury; group 1=animals treated with rhEPO protein (control); group 2=untreated animals (placebo group); group 3=animals treated with uncarbamoylated EPO-Fc fusion protein (comparative group); group 4=animals treated with carbamoylated EPO-Fc fusion protein (experimental group); group 5=animals treated with Methylprednisolon (comparative group).

FIG. 2 exhibits the results of the evaluation of an effect of carbamoylated EPO-Fc fusion protein in an Experimental Autoimmune Encephalomyelitis (EAE) mouse model at different stages of EAE progression by determination of the EAE score.

Ordinate=Experimental Autoimmune Encephalomyelitis (EAE) score scale; abscisse=days after starting administration.

DETAILED DESCRIPTION OF THE INVENTION

In its first embodiment, the present invention provides chemically modified, i.e. carbamoylated, recombinant EPO-Fc fusion proteins, having a significantly prolonged serum half-life as compared to unfused EPO proteins and, simultaneously, having a reduced hematopoietic activity relative to unmodified EPO-Fc fusion proteins plus a nerve cell regenerative activity that is unaltered or is even improved over the corresponding activity of the unmodified EPO or EPO-Fc fusion proteins.

"EPO-Fc fusion protein" as used herein refers to a protein comprising an EPO portion and an Fc portion. "EPO portion" as used herein encompasses full-length wildtype or naturally occurring erythropoietin from human or other sources, as well as erythropoietin-like molecules including biologically active erythropoietin fragments, analogs, variants, mutants and derivatives of erythropoietin. "Fc portion" as used herein encompasses domains derived from the constant region of an immunoglobulin, preferably from a human immunoglobulin, including a fragment, analog, variant, mutant or derivative of the constant region. Suitable immunoglobulins include IgG, i.e. the subclasses IgG1, IgG2, IgG3 and IgG4, and other classes.

The "biological activity" of erythropoietin referred to herein shall be understood as the ability of EPO or EPO-like molecules to interact with an erythropoietin receptor.

A biologically active EPO-like molecule typically shares substantial amino acid sequence similarity or identity (e.g. ranging from at least 55% to about 65%, 75%, 80%, and even up to about 90-95% identity) with the corresponding sequence of wild-type or naturally occurring EPO and possesses one or more of the functions of wildtype EPO.

As used herein, a "biologically active fragment" means a fragment that can exert a biological effect similar to the full length protein. Such fragments can be produced by amino- and carboxy-terminal deletions as well as by internal deletions. They also include truncated and hybrid forms of erythropoietin. "Truncated" forms are shorter versions of erythropoietin wherein one or more N-terminal and/or C-terminal residues are missing.

The EPO-Fc fusion protein of the present invention can be linked together in different ways. Either the Fc portion is linked via its C-terminus to the N-terminus of the EPO portion, i.e. the EPO-Fc fusion protein having a Fc portion towards the N-terminus of the EPO-Fc fusion protein, or as preferred in the present invention the Fc portion is linked via its N-terminus to the C-terminus of the EPO portion.

Further, the EPO portion and the Fc portion can be fused together either directly terminus by terminus, or indirectly via a linker, e.g. a peptide linker, inserted between the EPO portion and the Fc portion.

Accordingly, the present invention in a first aspect relates to a recombinant EPO fusion protein having an improved physiological half-life and a reduced hematopoietic activity as compared to EPO in vivo, and further having neuroregenerative activity in vivo, characterized in that it comprises an Fc portion of a human IgG molecule and an erythropoietin (EPO) portion, preferably a human erythropoietin portion, wherein the Fc portion is directly linked via its N-terminus to the C-terminus of the EPO portion and wherein the fusion protein is modified by carbamoylation.

In general, carbamoylation of proteins frequently occurs as a side effect of using urea in the purification of proteins and as a result of high urea serum levels by spontaneous decomposition of urea to cyanate. Cyanate is responsible for carbamoylation of primary amines including primary amines in proteins and readily reacts with the free amino residue of lysine and of the N-terminal amino acid of a protein, e.g. the EPO glycoprotein. The process of carbamoylation by cyanate is pH-dependent and can also occur, although to a lesser extent, with other amino acids of the protein including arginine, cysteine, tyrosine, aspartic acid, glutamic acid and histidine.

Preparative carbamoylation is carried out by reacting a predetermined amount of cyanate with a predetermined amount of protein. The degree of carbamoylation is dependent upon the reaction time between cyanate and protein and upon the concentration of cyanate and/or the desired protein.

In a further aspect the invention relates to such an EPO-Fc fusion protein, wherein at least one, preferably two or more, lysine residues and/or the N-terminal amino acid of said fusion protein are carbamoylated.

The carbamoylated EPO-Fc fusion protein of the present invention may contain additional modifications in the Fc portion, such as amino acid mutations like e.g. amino acid insertions, amino acid deletions or conservative or non-conservative amino acid substitutions. In particular, amino acid substitutions in the Fc portion are widely disclosed in the prior art to further extend the serum half-life of fusion proteins, e.g. EPO-Fc fusion proteins, by decreasing or eliminating Fc receptor binding or complement fixing activity. The EPO-Fc fusion protein may also have additional modifications in the erythropoietin portion such as amino acid mutations like e.g. amino acid insertions, amino acid deletions, conservative or non-conservative amino acid substitutions or amino acid deglycosylations which reduce the binding affinity for EPO receptor and/or increase the biological activity of erythropoietin.

In general, the constant region of an immunoglobulin is defined as a naturally-occurring or synthetically produced polypeptide homologous to the immunoglobulin C-terminal domain that is produced upon papain digestion. The constant region of an immunoglobulin heavy chain can include a heavy chain constant region 1 domain (CH1), a hinge region, a heavy chain constant region 2 domain (CH2) and a heavy chain constant region 3 domain (CH3).

Accordingly, the Fc portion of the present invention can include a hinge region, a CH2 and/or a CH3 domain. The Fc portion can further include the complete or a part of the hinge region, the CH2 and/or the CH3 domain.

In a further aspect the invention relates to such an EPO-Fc fusion protein which has an Fc portion comprising a hinge region, a CH2 domain and a CH3 domain derived from human IgG.

In a further aspect the invention relates to such an EPO-Fc fusion protein, wherein the fusion between the EPO portion and the Fc portion is accomplished at the hinge region.

In general, the EPO-Fc fusion protein of the present invention is produced by methods of recombinant expression, using techniques well known to those skilled in the art. In order to obtain a glycosylated recombinant EPO-Fc fusion protein having a glycosylation pattern, which is substantially the same as in naturally occurring EPO and immunoglobulins, it is preferred to use eukaryotic cells for the recombinant expression of the EPO-Fc fusion proteins. The recombinantly expressed proteins are secreted to the culture medium as single polypeptide chains to form EPO-Fc fusion protein monomers, but they can also be secreted to the culture medium in dimeric or multimeric form wherein the polypeptide chains are linked together via disulfide bonds.

In a further aspect the invention relates to such an EPO-Fc fusion protein, wherein two EPO-Fc fusion protein monomers are linked together to form a homodimer.

The secreted, recombinantly produced proteins can be isolated from the cell culture medium and further purified by techniques well known in the art.

In a further aspect the invention relates to a method for the preparation of a carbamoylated recombinant EPO-Fc fusion protein comprising a Fc portion of a human IgG molecule and an EPO portion, preferably a human EPO portion, wherein the Fc portion is directly linked via its N-terminus to the C-terminus of the EPO portion, the method comprising:
  preparing a DNA molecule encoding an EPO-Fc fusion protein;
  transforming a host cell with said DNA molecule;
  expressing said EPO-Fc fusion protein encoded by said DNA molecule;
  harvesting said EPO-Fc fusion protein;
  purifying said EPO-Fc fusion protein; and
  carbamoylating said EPO-Fc fusion protein by reacting said EPO-Fc fusion protein with cyanate,
wherein at least one, preferably two or more, lysine residues and/or the N-terminal amino acid of the fusion protein are carbamoylated.

The EPO-Fc fusion proteins of the present invention combine the advantageous prolonged serum half-life obtained by fusion of the EPO portion to the Fc portion of an immunoglobulin with a reduced hematopoietic activity while simultaneously maintaining an unaltered or even enhanced nerval cell regenerative activity due to the carbamoylation of at least one primary amine of the protein.

In a further aspect the invention relates to such an EPO-Fc fusion protein for use as a drug.

In general, such an EPO-Fc fusion protein can be used instead of carbamoylated EPO protein whenever treatment with carbamoylated EPO is required. Specifically, such an EPO-Fc fusion protein is used for the manufacture of a pharmaceutical composition for the treatment of a disease of the central nervous system (CNS) and/or the peripheral nervous system.

For example, such an EPO-Fc fusion protein can be used for the manufacture of a pharmaceutical composition for the treatment of a disease selected from the group consisting of a stroke, an ischemic event in the CNS other than a stroke, a contusion injury, a spinal cord injury, a traumatic brain injury, and a neurodegenerative disease.

Due to the prolonged serum half-life of the inventive EPO-Fc fusion proteins as compared to carbamoylated unfused EPO proteins, pharmaceutical compositions containing such EPO-Fc fusion proteins require less frequent administration as compared to pharmaceutical compositions containing carbamoylated unfused EPO proteins. Therefore a therapy with the EPO-Fc fusion proteins of the present invention is much more comfortable for a patient requiring such a treatment.

In a further aspect the invention relates to a pharmaceutical composition comprising such a EPO-Fc fusion protein, optionally together with a pharmaceutically acceptable carrier.

In a further aspect the invention relates but is not limited to such a pharmaceutical composition suitable for parenteral administration. Since efficient EPO therapy requires therapeutic EPO serum levels it is desirable that such pharmaceutical compositions are adapted as an injection solution wherein the EPO-Fc fusion protein of the present invention is present in admixture with pharmaceutically acceptable carrier substances. In a preferred embodiment of the present invention such pharmaceutical compositions are provided in a galenic form suitable for intravenous or subcutaneous injection.

In a further aspect the invention relates to the use of such pharmaceutical compositions for the treatment of a disease of the central nervous system (CNS) and/or the peripheral nervous system.

In a further aspect the invention relates to the use of such pharmaceutical compositions for the treatment of a disease selected from the group consisting of a stroke, an ischemic event in the CNS other than a stroke, a contusion injury, a spinal cord injury, a traumatic brain injury, and a neurodegenerative disease.

In order that the invention described herein may be more fully understood, the following examples are set forth. The examples are for illustrative purposes only and are not to be construed as limiting this invention in any respect.

EXAMPLES

Example 1

Preparation and Characterisation of Carbamoylated EPO-Fc Fusion Proteins a) Construction of an Expression Vector Encoding EPO-Fc Fusion Protein:

The Epo-Fc fusion protein was generated by fusion-PCR of the human EPO gene and a human IgG1 hinge-CH2-CH3 fragment. The EPO was set at the N-terminus of the construct and fused to the hinge region of the human IgG1. For secretion of the protein into the culture supernatant the erythropoietin signalling sequence was used that was amplified together with the EPO cDNA. This construction enables the secretion of a homodimeric EPO-Fc molecule.

Human Epo cDNA was amplified from the plasmid phEpo by PCR using the oligonucleotides epo back BamHI (designed to append a unique BamHI restriction site onto the 5' end of the DNA fragment) and epo hyb hinge for resulting in a 576 bp DNA fragment (epo back BamHI: 5' GGGGGATC-CGCC ATGGGGGTGCACGAATGTCC 3' [SEQ ID NO 1]; epo hyb hinge for: 5' AGATTTGGGCTCTCTGTCCCCT-GTCCTGCAGG 3' [SEQ ID NO 2]). The human IgG1 hinge-CH2-CH3 fragment was amplified from the plasmid p2G12HC by PCR using the oligonucleotides CH3 for NotI (designed to append a unique NotI restriction site onto the 3' end of the DNA fragment) and hinge hyb epo back resulting in a 671 bp DNA fragment (CH3 for NotI: 5' GGGGCGGC-CGCTCAT TTACCCGGAGACAGG 3' [SEQ ID NO 3]; hinge hyb epo back: 5' ACAGG GGACAGAGAGC-CCAAATCTTGTGAC 3' [SEQ ID NO 4)]: Amplification was carried out in a total volume of 50 µl using 20 ng plasmid template, 10 µmol of each oligonucleotide, 250 µM nucleotides, 1×PCR buffer and 5 units of the thermostable Taq polymerase. Both PCR reactions were performed for 25 cycles with 94° C. for 20 sec, 56° C. for 30 sec and 72° C. for 1 min.

After purification of the two fragments with Qiaquick purification kit (Qiagen) the fusion PCR was performed in 50 µl volume using 50 ng IgG1 hinge-CH2-CH3 cDNA, 50 ng EPO cDNA, 250 µM nucleotides, 1×PCR buffer and 5 units Taq polymerase. In a first step 6 cycles were done with 94° C. for 20 sec, 60° C. for 30 sec and 72° C. for 1 min. After adding 10 µmol of each of the outer primers (epo back BamHI and CH3 for NotI) the PCR was continued for 25 cycles with 94° C. for 20 sec, 56° C. for 30 sec and 72° C. for 1.5 min.

Afterwards the PCR product was purified by preparative gel extraction and gel extraction kit from Qiagen. The resulting EPO-Fc cDNA was inserted into a BamHI/NotI opened eukaryotic expression vector containing the human CMV (cytomegalo virus) promoter and transformed into E. coli strain TG1. 10 ng of EPO-Fc fragment and 5 ng of pECMV vector, 1 unit of T4-ligase and 1× ligation buffer (New England Biolabs) were used for ligation in 10 µl of total volume for 1 hour at 37° C. Positive clones were identified by PCR-screening with the outer primers. The correctness of the Epo-Fc cDNA in the final plasmid pCMV_EpoFc was verified by sequence and restriction analysis.

b) EPO-Fc Fusion Protein Expression and Purification:

The large scale plasmid preparation (pCMV_EpoFc) from step a) was used for transfection of dihydrofolate-reductase negative CHO cells. The two plasmids pCMV_EpoFc and p2_dhfr were used in a 20:1 ratio for transfection of cells with lipofectin. Selection of transfected cells was started 24 hours after transfection (DMEM 4 mM L-Glutamine and 10% dialysed FCS) and MTX pressure was applied (0.05 µM and 0.1 µM MTX) when clones started to grow. After selection and isolation of the best performing clone cultivation was switched to protein free conditions. The cell supernatant is harvested from a fed batch fermentation with a cell viability of 80%.

The supernatant is size filtered (0.2 µm pore size) and 1 M Tris is added to a final pH of 8.5 and then passed over a protein A-Sepharose column equilibrated with 0.025 M Tris-buffered saline, pH 8.5 and eluted with 0.1 M glycine, pH 3.5. The pH of eluted product fraction was pH measured and set to pH 7.0-7.5 with 1 M Tris, pH 8.0, if necessary.

c) Production of Carbamoylated EPO-Fc Fusion Protein:

The starting material for this process was purified recombinant human EPO-Fc fusion protein as described above, typically including all isoforms of the fusion protein present in the culture supernatant, which allows for a high yield of the desired end product.

First the protein concentration of the recombinant human EPO-Fc fusion protein was adjusted to 4-7 mg/ml by Ultra-filtration (e.g. membrane with 10 kD cut off). A KOCN-borate solution was prepared by dissolving 60 mg/mg$_{EPO\text{-}Fc\,fusion\,protein}$ in 0.6 M Na-borate buffer, pH 8.

Then the EPO-Fc fusion protein solution was mixed with the KOCN-borate solution in a ratio of 1:1 and the solution was incubated for 48 hours at 37° C. The carbamoylated EPO-Fc fusion protein was endformulated by gelfiltration (e.g. Sephadex G25) in PBS. The concentration of carbamoylated EPO-Fc fusion protein was determined by $OD_{280nm}$ according to a calibration curve with EPO-Fc fusion protein, which was determined by ELISA.

Subsequent determination of the degree of carbamoylation confirmed that substantially all free amino groups were carbamoylated.

Example 2

Determination of Locomotor Recovery in Rats after Contusion Injury

In an animal experiment the in vivo nervel cell regenerative activity of carbamoylated EPO-Fc fusion protein in comparison to unmodified EPO-Fc fusion protein was analysed. Carbamoylated EPO-Fc fusion protein and unmodified EPO-Fc fusion protein were produced as disclosed in Example 1.

35 Sprague-Dawley rats weighing 240-260 g were divided in five groups comprising six animals (group 1), seven animals (group 2, 4 and 5) or eight animals (group 3). The animals were anaesthetized with a mixture of Ketavet (110 mg/kg) and Rompun (12 mg/kg) injected intraperitoneally followed by a laminectomy at the T-11 level. After the spinal cord was exposed the animals received a spinal cord contusion injury of 150 kdyne by using the IH 400 Impactor (Precision Systems & Instrumentation, Lexington, Ky., USA). One hour after injury the animals received a single dose injection of the respective protein (see table 1). Locomotor recovery was assessed by the Basso-Beattie-Bresnahan rating scale three days, one week, two weeks, three weeks, four weeks, five weeks and six weeks after the contusion injury event. The Basso-Beattie-Bresnahan rating scale is a 21-point scale that systematically details hind limb function of joint movements, stepping ability, the degree of fine control of coordinated stepping and trunk stability.

TABLE 1

| Group arrangement of the mice study | |
|---|---|
| group 1 | treated with 1000 units/kg (equivalent 10 µg/kg) of recombinant human EPO (rhEPO); control group |
| group 2 | treated with NaCl i.p.; placebo group |
| group 3 | treated with 30 µg/kg of rhEPO-Fc |
| group 4 | treated with 30 µg/kg of carbamoylated rhEPO-Fc |
| group 5 | treated with 30 mg/kg of Methylprednisolone (MPSS) |

Figure 1:
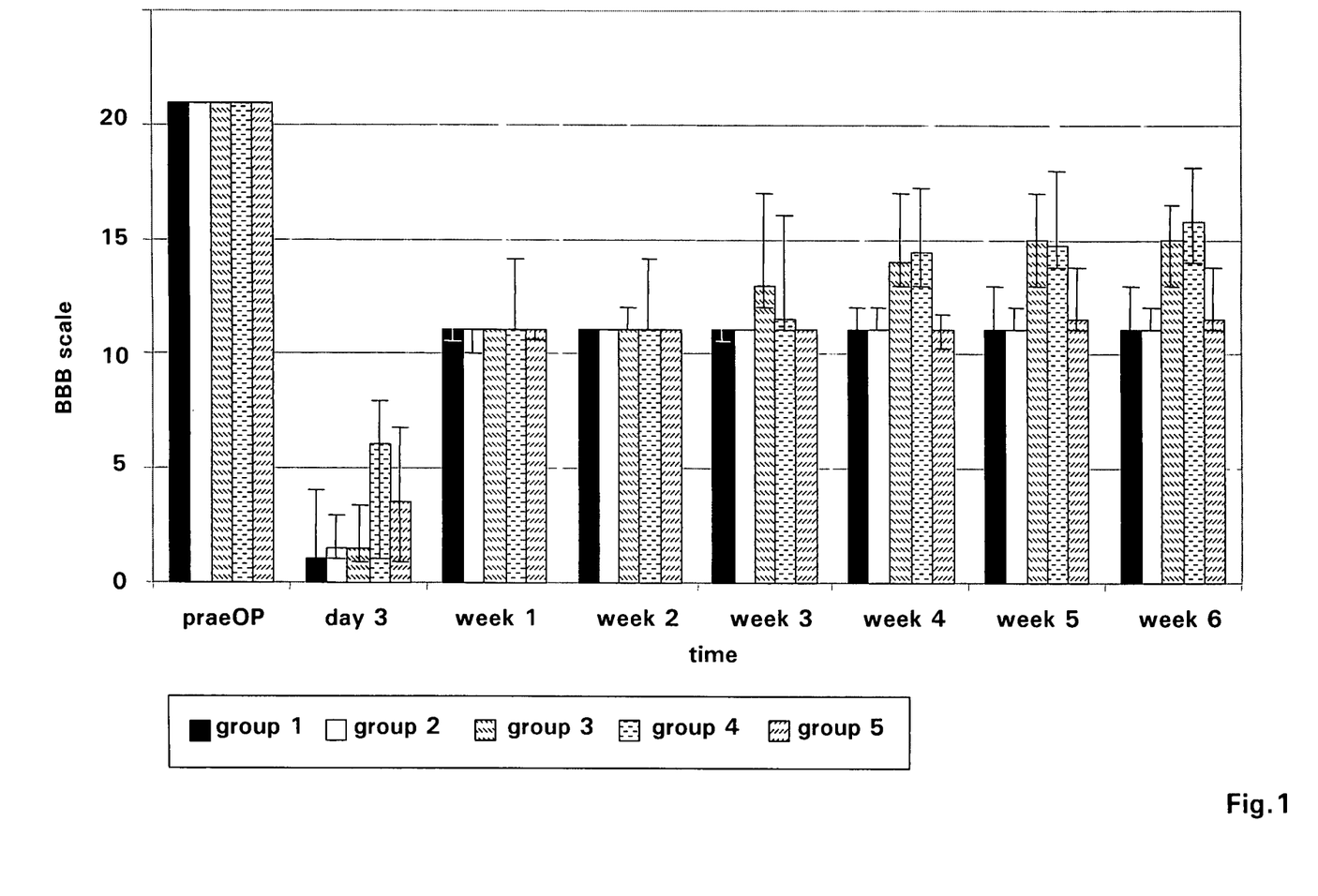
FIG. 1 exhibits the results of the determination of locomotor recovery in rats after contusion injury, upon subsequent administration of carbamoylated EPO-Fc fusion protein according to the present invention.

Animals were exposed in an open field and were observed during a five minute period three days, one week, two weeks, three weeks, four weeks, five weeks and six weeks after the contusion injury event. FIG. 1 discloses the values on the Basso-Beattie-Bresnahan scale obtained in this experiment.

It was found that administration of carbamoylated rhEPO-Fc (group 4) and rhEPO-Fc (group 3) significantly improves locomotor recovery as compared to the control groups (groups 1 and 2). In contrast thereto animals treated with methylprednisolone (group 5) hardly show any difference to the control animals. While the control animals reach a steady state after approximately four weeks and do not show any regenerative improvement further, the animals of groups 3 and 4 (EPO-Fc fusion protein and carbamoylated EPO-Fc fusion protein, respectively) show continuous and significant improvements over the six-weeks recovery period.

It was also found that administration of carbamoylated rhEPO-Fc (group 4) significantly improves locomotor recovery as compared to rhEPO-Fc (group 3), in particular shortly after contusion injury. At day three animals treated with rhEPO-Fc showed only extensive movement of one joint or two joints (value 2 or 3 on the Basso-Beattie-Bresnahan rating scale, respectively) while animals treated with carbamoylated rhEPO-Fc showed extensive movement of at least two joints and slight movement of the third joint or extensive movement of all three joints of the hind limb (value 6 or 7 on the Basso-Beattie-Bresnahan rating scale, respectively).

Example 3

Evaluation of the Effect of Carbamoylated EPO-Fc Fusion Protein in a Mouse Model of Multiple Sclerosis In an animal experiment the in vivo effect of carbamoylated EPO-Fc fusion protein in the early, intermediate and late phase of Experimental Autoimmune Encephalomyelitis (EAE) progression was analysed. EAE can be induced in rodents e.g. in mice and is a widely accepted animal model for demyelinating disorders like Multiple Sclerosis (MS). The EAE mouse model mimics the relapsing and remitting course typical of MS.

Carbamoylated EPO-Fc fusion protein used in this experiment was produced as disclosed in Example 1.

EAE was induced in 11 C57BL/6 female mice by immunization with Myelin Oligodendrocyte Glycoprotein ($MOG_{35-55}$) (Savino, C. et al. (2006) J Neuroimmunol 172 (1-2):27-37). In brief, a 4 mg/ml solution of $MOG_{35-55}$ was prepared in PBS. Heat killed *Mycobacterium tuberculosis* (Difco H37RA) was suspended in Incomplete Freund's Adjuvant (IFA) to a concentration of 8 mg/ml. The suspension was emulsified with the $MOG_{35-55}$ solution. 100 μl of this emulsion were then injected subcutaneously in each mouse, 50 μl in either flank. Finally, 250 ng of Pertussis toxin dissolved in PBS were injected intravenously twice in each animal, once directly after immunization and once 48 hours after immunization.

To analyse the effect of carbamoylated EPO-Fc fusion protein at different stages of EAE progression the EAE induced animals were divided into a test group (five animals) and a control group (six animals). The animals of the test group were treated with carbamoylated EPO-Fc fusion protein at a dose of 50 μg/kg body weight whereas the control group received PBS only. Administration by intraperitoneal injection of either carbamoylated EPO-Fc fusion protein or PBS was started 18 days (early treatment), 28 days (intermediate treatment) or 52 days (late treatment) after immunization. Thereto, each the test group and the control group were further divided in three subgroups (see Table 2). The treatment was carried out for 30 days and the animals received a dose every alternate day.

TABLE 2

Group arrangement of the mice study

| | | |
|---|---|---|
| early treatment (starting administration 18 days after immunization) | group 1 (three animals) | treated with carbamoylated EPO-Fc fusion protein at a dose of 50 μg/kg body weight; test group |
| | group 2 (three animals) | treated with PBS; control group |
| intermediate treatment (starting administration 28 days after immunization) | group 3 (one animal) | treated with carbamoylated EPO-Fc fusion protein at a dose of 50 μg/kg body weight; test group |
| | group 4 (two animals) | treated with PBS; control group |
| late treatment (starting administration 52 days after immunization) | group 5 (one animal) | treated with carbamoylated EPO-Fc fusion protein at a dose of 50 μg/kg body weight; test group |
| | group 6 (one animal) | treated with PBS; control group |

The clinical condition of the animals and the progression of the disease were monitored. Thereto, the neurological deficits exhibited by the animals were assessed quantitatively by the EAE score every day during treatment according to the grading system shown in Table 3 (Buddeberg, B. S. et al. (2004) J Neuroimmunol 153(1-2):158-70).

TABLE 3

EAE Score

| score | clinical signs of disease |
|---|---|
| 0 | no clinical abnormality |
| 0.5 | partial tail weakness or slight loss of muscle tone |
| 1 | tail weakness |
| 1.5 | slightly clumsy gait |
| 2 | hind limb paresis |
| 2.5 | hind limb paresis and partial dragging of the hind limbs |
| 3 | hind limb paralysis |
| 3.5 | hind limb paralysis and forelimb paresis |
| 4 | paralysis (tetraplegy) |
| 5 | moribund or dead |

Figure 2A:
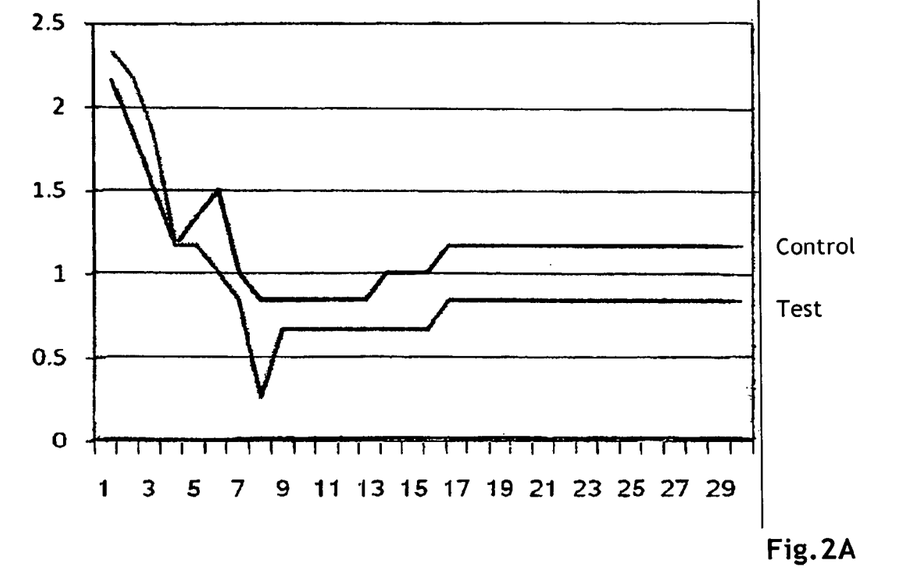
FIG. 2A=early treatment: animals treated with either carbamoylated EPO-Fc fusion protein (Test; group 1) or PBS (Control; group 2), administration was started on day 18 after EAE induction.
Figure 2B:
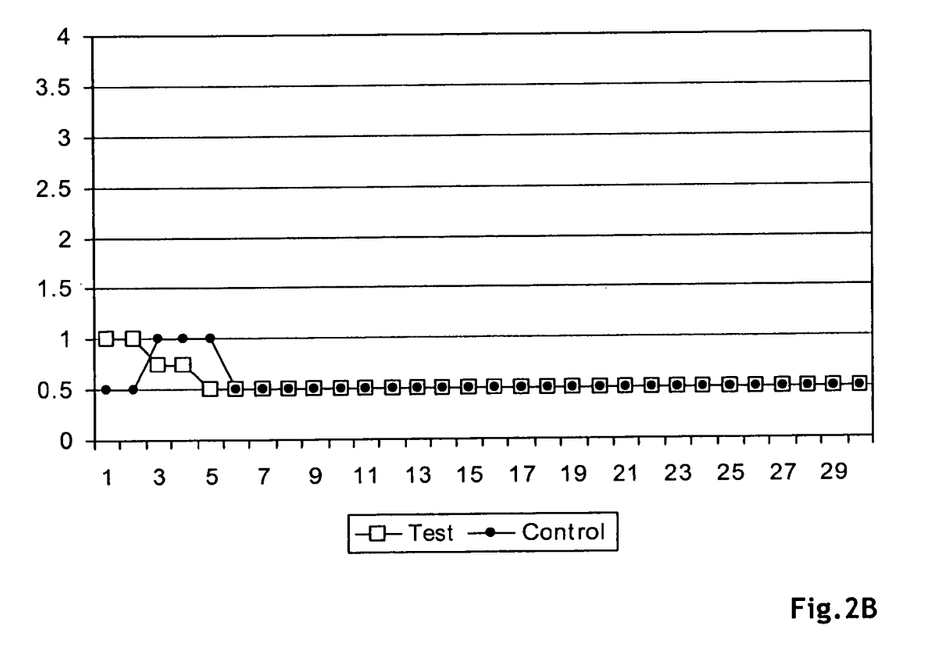
FIG. 2B=intermediate treatment: animals treated with either carbamoylated EPO-Fc fusion protein (Test; group 3) or PBS (Control; group 4), administration was started on day 28 after EAE induction.
Figure 2C:
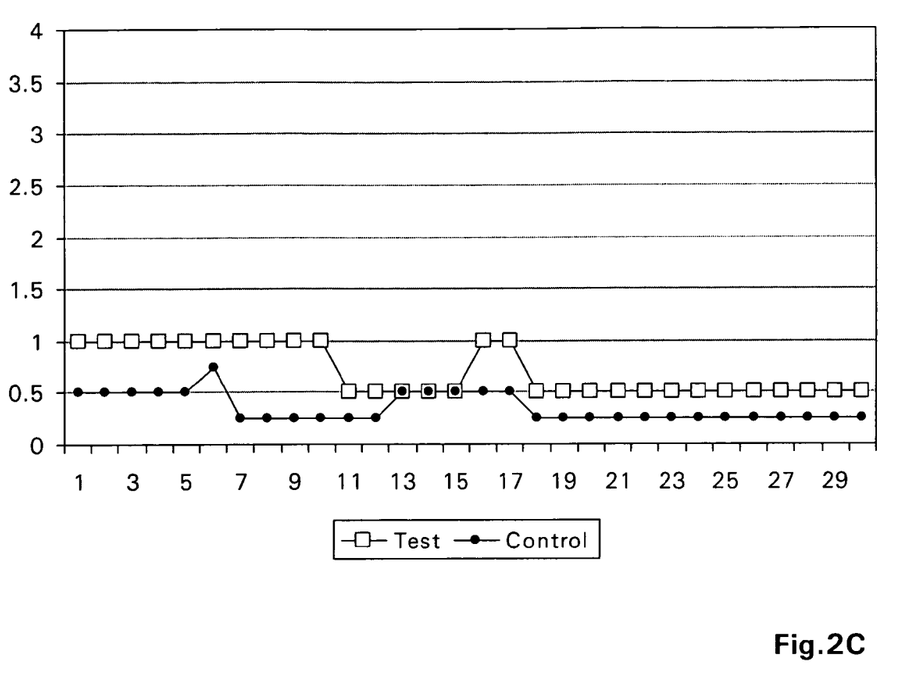
FIG. 2C=late treatment: animals treated with either carbamoylated EPO-Fc fusion protein (Test; group 5) or PBS (Control; group 6), administration was started on day 52 after EAE induction. Detailed information about the mice group arrangement is found in Table 2. The FIGS. 2A to 2C show the average EAE score of the animals used in each group.

FIGS. 2A to 2C disclose the EAE scores obtained from these animal experiments, whereby each Figure shows the average score of the animals used in each group.

It was found that administration of carbamoylated EPO-Fc fusion protein (groups 1, 3 and 5) reduces the relapse rates in the early (FIG. 2A), the intermediate (FIG. 2B) and the late phase (FIG. 2C) of EAE progression as compared to the control (groups 2, 4 and 6). While the EAE scores of the control animals were oscillating up and down it was observed for the animals treated with carbamoylated EPO-Fc fusion protein that the EAE score, i.e. the intensity of the disease, never went higher than at the beginning of the treatment.

It was also found that early administration of carbamoylated EPO-Fc fusion protein (FIG. 2A) has a better effect on EAE progression than late administration of carbamoylated EPO-Fc fusion protein (FIG. 2C) when compared with the respective control. More specifically, it can be seen from FIG. 2A that at day 30 after beginning of administration the average score of the animals treated with carbamoylated EPO-Fc fusion protein (Test) decreased by 65.2%, whereas the average score of the control animals only decreased by 46.1%.

The results from these experiments suggest a positive effect of carbamoylated EPO-Fc fusion protein on EAE progression.

We claim:

1. A recombinant erythropoietin (EPO)-Fc fusion protein comprising:
   an EPO portion; and
   an Fe portion of a human IgG molecule directly linked via its N-terminus to the C-terminus of the EPO portion,
   wherein:
   the fusion protein is modified by carbamoylation;
   the fusion protein comprises substantially all fusion protein isoforms present in a supernatant of a cell culture expressing the fusion protein;
   the fusion protein has neuroregenerative activity in vivo; and
   the fusion protein has an improved physiological half-life and a reduced hematopoietic activity as compared to EPO in vivo.

2. The fusion protein according to claim 1, comprising all fusion protein isoforms present in the supernatant of the cell culture expressing the fusion protein.

3. The fusion protein according to claim 1, wherein one or more lysine residues and/or the N-terminal amino acid of the fusion protein are carbamoylated.

4. The fusion protein according to claim 1, wherein the Fe portion comprises a hinge region, a CH2 domain and a CH3 domain derived from human IgG, and fusion is at the hinge region.

5. The fusion protein according to claim 1, wherein two EPO-Fc fusion protein monomers are linked together to form a homodimer.

6. The fusion protein according to claim 1, wherein the EPO portion is a human EPO portion.

7. The fusion protein according to claim 1 for use as a drug.

8. A pharmaceutical composition comprising the fusion protein according to claim 1 and a pharmaceutically acceptable carrier.

9. The pharmaceutical composition according to claim 8, wherein the pharmaceutical composition is an injection solution.

10. A method for preparing a carbamoylated recombinant EPO-Fc fusion protein comprising an EPO portion and an Fe portion of a human IgG molecule directly linked via its N-terminus to the C-terminus of the EPO portion, the method comprising:
    preparing a DNA molecule encoding an EPO-Fc fusion protein;

transforming a host cell with the DNA molecule;
expressing the EPO-Fc fusion protein encoded by the DNA molecule by culturing the transformed host cell in a cell culture medium so as to secrete the EPO-Fc fusion protein into the cell culture medium;
collecting a supernatant from the cell culture medium containing the EPO-Fc fusion protein;
purifying the EPO-Fc fusion protein such that the EPO-Fc fusion protein comprises substantially all EPO-Fc fusion protein isoforms in the supernatant; and
carbamoylating the purified EPO-Fc fusion protein by reacting an amount of cyanate with an amount of the purified EPO-Fc fusion protein such that one or more lysine residues and/or the N-terminal amino acid of the EPO-Fc fusion protein are carbamoylated,
wherein the carbamoylated EPO-Fc fusion protein has reduced hematopoietic activity and unaltered or enhanced neuroregenerative activity in vivo as compared to an uncarbamoylated EPO-Fc fusion protein.

11. The method according to claim 10, wherein the EPO-Fc fusion protein is purified such that the EPO-Fc fusion protein comprises all EPO-Fc fusion protein isoforms in the supernatant.

12. The method according to claim 10, wherein the Fc portion comprises a hinge region, a CH2 domain and a CH3 domain, and fusion is at the hinge region.

13. A method for preparing a pharmaceutical composition comprising a carbamoylated recombinant EPO-Fc fusion protein comprising an EPO portion and an Fe portion of a human IgG molecule directly linked via its N-terminus to the C-terminus of the EPO portion, the method comprising:
preparing a DNA molecule encoding an EPO-Fc fusion protein;
transforming a host cell with the DNA molecule;
expressing the EPO-Fc fusion protein encoded by the DNA molecule by culturing the transformed host cell in a cell culture medium so as to secrete the EPO-Fc fusion protein into the cell culture medium;
collecting a supernatant from the cell culture medium containing the EPO-Fe fusion protein;
purifying the EPO-Fc fusion protein such that the EPO-Fc fusion protein comprises substantially all EPO-Fc fusion protein isoforms in the supernatant;
carbamoylating the purified EPO-Fc fusion protein by reacting an amount of cyanate with an amount of the purified EPO-Fc fusion protein such that one or more lysine residues and/or the N-terminal amino acid of the EPO-Fc fusion protein are carbamoylated;
purifying the carbamoylated EPO-Fc fusion protein by gel filtration without any further purification; and
mixing the purified carbamoylated EPO-Fc fusion protein with a pharmaceutically acceptable carrier,
wherein the carbamoylated EPO-Fc fusion protein has reduced hematopoietic activity and unaltered or enhanced neuroregenerative activity in vivo as compared to an uncarbamoylated EPO-Fc fusion protein.

14. The method according to claim 13, wherein the EPO-Fc fusion protein is purified such that the EPO-Fc fusion protein comprises all EPO-Fc fusion protein isoforms in the supernatant.

15. The method according to claim 13, wherein the Fc portion comprises a hinge region, a CH2 domain and a CH3 domain, and fusion is at the hinge region.

16. The method according to claim 13, wherein the pharmaceutical composition is formulated for parenteral administration.

17. The method according to claim 13, wherein the pharmaceutical composition is formulated for intravenous or subcutaneous injection.

18. A pharmaceutical composition obtained by the method according to claim 17.

19. A pharmaceutical composition obtained by the method according to claim 13.

20. A method of treating a disease of the central nervous system (CNS) and/or the peripheral nervous system comprising administering to a subject a composition comprising the fusion protein according to claim 1, wherein the disease is selected from the group consisting of a stroke, a contusion injury, multiple sclerosis, a spinal cord injury, and a traumatic brain injury.

21. The method according to claim 20, wherein the disease is a spinal cord injury.

22. A method of treating a disease of the central nervous system (CNS) and/or the peripheral nervous system comprising administering to a subject the pharmaceutical composition according to claim 19, wherein the disease is selected from the group consisting of a stroke, a contusion injury, multiple sclerosis, a spinal cord injury, and a traumatic brain injury.

23. The method according to claim 22, wherein the disease is a spinal cord injury.

* * * * *